US00PP28750P2

(12) United States Plant Patent
Hansen

(10) Patent No.: US PP28,750 P2
(45) Date of Patent: Dec. 5, 2017

(54) ×*HEUCHERELLA* PLANT NAMED 'HOPSCOTCH'

(50) Latin Name: ×*Heucherella (Heuchera×Tiarella)*
Varietal Denomination: Hopscotch

(71) Applicant: Hans A. Hansen, Zeeland, MI (US)

(72) Inventor: Hans A. Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 15/530,091

(22) Filed: Dec. 1, 2016

(51) Int. Cl.
*A01H 5/02* (2006.01)

(52) U.S. Cl.
USPC ..... Plt./441

(58) Field of Classification Search
USPC ..... Plt./441
CPC ..... A01H 5/02; A01H 5/12
See application file for complete search history.

*Primary Examiner* — Kent L Bell

(57) ABSTRACT

The new hybrid ×*Heucherella* plant named 'Hopscotch' with deeply incised palmately lobed foliage of variable coloration starting in the spring as red with dark red centers, transitioning to bronze-red during flowering and deep green in winter. 'Hopscotch' begins flowering in late spring with a creamy-white effect.

1 Drawing Sheet

Botanical denomination: ×*Heucherella* (*Heuchera*× *Tiarella*).

Cultivar designation: 'Hopscotch'.

BACKGROUND OF THE INVENTION

The present invention relates to a new and distinct intergeneric hybrid between Coral Bells and Foam Flower, both in the Saxifragaceae family and given the cultivar name of 'Hopscotch' with the combined generic epithet ×*Heucherella.* ×*Heucherella* 'Hopscotch' resulted from an intentional cross between the unreleased proprietary *Heuchera* hybrid known by the breeder code K10-74-23 (not patented) as the female or seed parent and *Tiarella* 'Jade Peacock' U.S. Plant Pat. No. 26,730 as the male or pollen parent. The new plant was hybridized by Hans A. Hansen at a wholesale perennial nursery in Zeeland, Mich., USA on Feb. 11, 2013 and harvested in the spring of 2013. The new plant passed the original evaluation in summer 2013 and was given the breeder code of 13-212-6. The new plant was selected from among many other crosses and ×*Heucherella* seedlings growing at the same nursery in Zeeland, Mich. which met the rigorous criteria of excellent foliage and habit established as breeding goals. ×*Heucherella* 'Hopscotch' has been asexually propagated since 2014 by division of the rhizome at a nursery in Zeeland, Mich. and also by careful tissue culture propagation. The resultant asexually propagated plants have remained stable and exhibit the same characteristics as the original plant.

No plants of ×*Heucherella* 'Hopscotch' have been sold, under this or any name, in this country or anywhere in the world, prior to the filing of this application, nor has any disclosure of the new plant been made prior to the filing of this application with the exception of that which may have been disclosed within one year of the filing of this application and was either derived directly or indirectly from the inventor.

BRIEF SUMMARY OF THE INVENTION

×*Heucherella* 'Hopscotch' differs from its parents as well as all other ×*Heucherella* known to the applicant. Compared to the female parent, the new plant has creamy-white flowers, the foliage more deeply dissected with longer lobes, and the foliage color is more reddish-bronze. Compared to the male parent, the new plant has more reddish bronze foliage with deeper-cleft and rounded lobes and the flowers are creamy-white rather than light pink. The most similar cultivars include: ×*Heucherella* 'Burnished Bronze' U.S. Plant Pat. No. 12,159, 'Autumn Cascade' U.S. Plant Pat. No. 27,569 and 'Sweet Tea' U.S. Plant Pat. No. 21,296.

Compared to 'Sweet Tea', the new plant has deeper cleft foliage with more rounded lobes. Compared to 'Burnished Bronze' the new plant has more deeply cleft leaf blades with more rounded lobes, and the coloration is more bronze rather than the reddish of 'Burnished Bronze'. The new plant has foliage that is more deeply cleft with rounded lobes than 'Autumn Cascade', and the habit is more clumping and less trailing.

The new plant differs from all *Heuchera,* ×*Heucherella* and *Tiarella* known to the inventor in the following combined traits:

1. The foliage color of ×Heucherella 'Hopscotch' is variable with the seasons starting in the spring with red with dark red centers.
2. Leaves transition from reddish to bronze red shortly after emerging and late in the season become deep green.
3. The leaf blade shape is deeply cleft with rounded lobes.
4. The flowers are creamy-white and tightly arranged on panicles just over the foliage with repeat flowering over an extended period from late spring through summer.
5. Habit is mounded with multiple tightly clustered shoots emerging at the base all season.
6. The plant is robust, seedless, compact and is more heat and sun tolerant than typical ×*Heucherella.*

BRIEF DESCRIPTION OF THE DRAWINGS

The photographs of the new plant demonstrate the overall appearance of the plant including the unique traits. The plant in the photograph is of a two-year old plant grown in a double-poly coated greenhouse without further shading, with supplemental fertilizer and water as needed at a wholesale perennial nursery in Zeeland, Mich., USA. The colors are as accurate as reasonably possible with color reproductions. Some slight variation of color may occur as a result of lighting quality, intensity, wavelength, and direction or reflection.

DETAILED BOTANICAL DESCRIPTION

Figure 1:
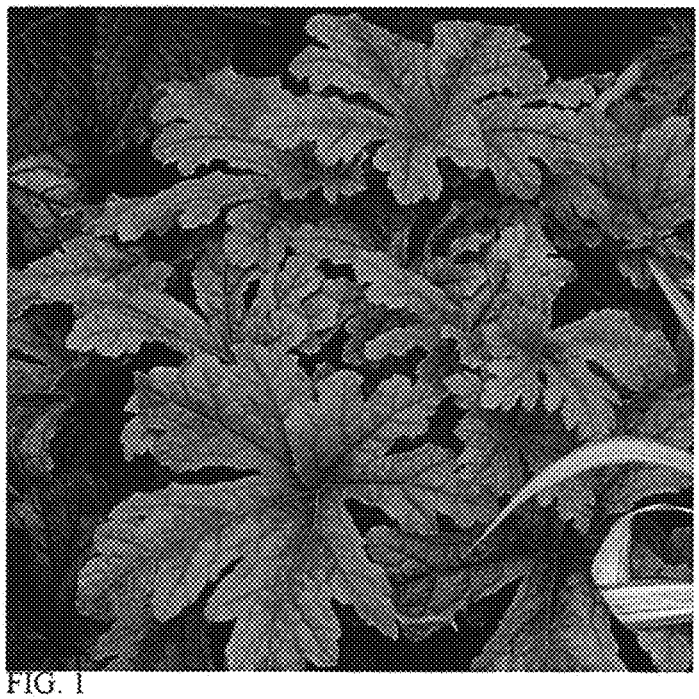
FIG. 1 shows a close-up of the foliage in the greenhouse in mid-season coloration.
Figure 2:
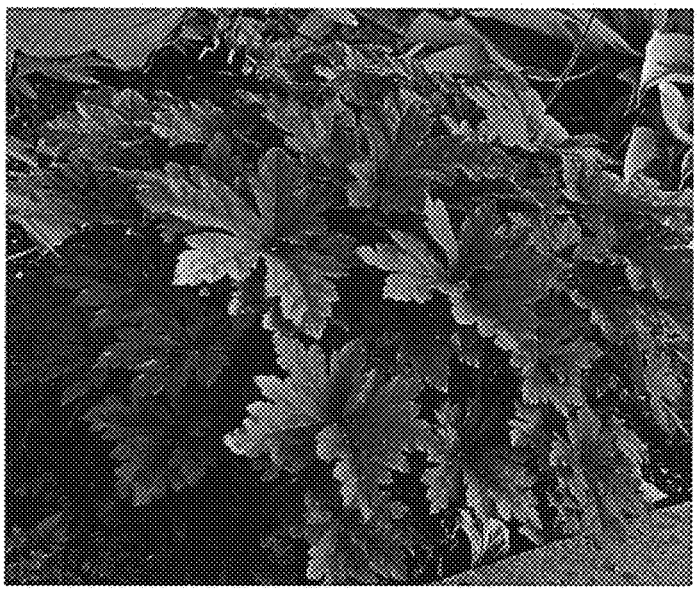
FIG. 2 shows a two-year-old plant in a shaded trial garden in Zeeland, Mich. in mid-spring flowering.

The following description is based on two-year-old plants growing in double poly greenhouse with supplemental water and fertilizer at a wholesale perennial nursery in Zeeland, Mich., USA. the new plant has not been grown under all possible environments and may phenotypically appear different under different conditions such as light, temperatures, fertilizer, and water, without any difference in genotype. The color descriptions are from the 2001 edition of The Royal Horticultural Society Colour Chart except where common dictionary terms are used.

Parentage: Unreleased proprietary *Heuchera* hybrid K10-74-23 as the female (seed parent); *Tiarella* 'Jade Peacock' as the male (pollen).

Plant habit: Hardy herbaceous perennial of tightly compact rhizomes with basal rosette of mounded foliage; foliage about 25 cm tall and 50 cm in diameter.

Roots: Fibrous, finely branched; when actively growing near white in color depending on soil type.

Growth rate: Rapid, rooting from cutting in 2 weeks and finishing in three-liter container in about 3 months; beginning to flower in 6 to 8 weeks following a 9 week vernalization.

Foliage: Leaf blade hirsutulous above and sparsely hirsutulous below; palmately five-lobed to six-lobed, lobes incised typically to more than four-fifths of the way to petiole; matte surface above and slightly lustrous below; nearly rounded lobe apices with apices and margin crenate to mucronulate, and cordate base with lobes imbricate to about 1.0 cm; blade to about 12.5 cm long and 14.5 cm wide, average about 10.5 cm long and 11.0 cm wide; center lobe to about 8.5 cm long, average about 6.5 cm long.

Foliage color: Leaf color is seasonally variable; young spring and expanding leaves adaxial between RHS 60 B and RHS 60C center of lobes, nearest RHS 174C with tint of nearest RHS 186C toward margin and between margin and center blend between RHS N187D and RHS 186D; expanding abaxial blend between RHS N187D and RHS 186D toward center with margin nearest RHS 174D with tint of RHS 186C; at flowering adaxial nearest RHS 175B toward center and 173A toward margin with other leaves nearest RHS 152A, at flowering abaxial some leaves nearest RHS 182B and others nearest RHS 152A; winter leaves adaxial mixtures of RHS 152A, RHS 165B and RHS 166B, winter abaxial nearest RHS 176B with green undertone of nearest RHS 152A.

Leaf margin: Serrulate.

Leaf apex: Acute.

Leaf base: Cordate with frequently imbricate lobes.

Leaf surface: Pubescent adaxial and abaxial.

Leaf quantity: Dense, about seven per division and 250 per plant.

Veins: Palmate, pubescent adaxial and abaxial.

Vein color: Adaxial expanding foliage between RHS 165D and RHS 165C and abaxial nearest RHS 199D; at time flowering adaxial main veins nearest RHS N170B and outer smaller veins nearest RHS 178B, at time of beginning flowering abaxial main veins nearest RHS 182D; winter adaxial veins nearest RHS 177B and overwintered abaxial nearest RHS 182C.

Petiole: Terete, pubescent, base clasping; to 19.5 cm long and 3.0 mm diameter base; average about 16.0 cm long and 2.5 mm diameter at base; wiry but flexible.

Petiole color: On emerging foliage nearest RHS 187D toward base with distal nearest RHS 186B with blend of nearest RHS 157B; at flowering between RHS 187C and RHS 187B; winter between RHS 183C and RHS 183D.

Inflorescence: In branched panicle, about eight racemes per plant; about 150 flowers per panicle; first panicle flowering beginning in late spring with repeat racemes flowering into summer; individual panicles remaining in flower for about three to four weeks; flower attitude mostly outwards.

Fragrance: None detected.

Peduncle: Terete, erect; glandular, puberulent; to about 50.0 cm tall and 3.0 mm diameter at base; flowering portion about 28.0 cm long and 5.5 cm across.

Peduncle attitude: Upright; erect.

Peduncle branches: In lower two thirds of peduncle with average of 3.5 flowers per branch on 34 branches; branches to about 11.0 cm long and about 0.7 mm diameter at base.

Peduncle color: Distal region nearest RHS N186C and basal region nearest RHS186B.

Pedicel: Terete; puberulent to glandular; to about 6.0 mm long and 0.5 mm in diameter, average about 4.0 mm long and 0.5 mm diameter at base.

Pedicel color: Nearest RHS 187C.

Buds one day prior to opening: Ellipsoid with acute apex, about 3.0 mm long and 2.0 mm diameter.

Bud color: Nearest RHS 158A tinted with nearest RHS 186A.

Flower: Perfect, campanulate, actinomorphic; about 6.0 mm deep and 8.5 mm in diameter at face; individual flowers lasting about three to four days on plant or as cut raceme.

Calyx: Five sepals; glandular abaxial, glabrous adaxial; apex acute, fused at base into hypanthium; margin entire; sepals about 6.0 mm long and 1.5 mm wide at point of fusion.

Calyx color: Abaxial nearest RHS N155C with glandular hairs nearest RHS 187C; adaxial near white nearest RHS 155D.

Petals: Five; adnate to calyx; spatulate, acute apex, attenuate base; margin entire; puberulent outside and glabrous inside; about 4.0 mm long and 0.8 mm wide.

Petal color: Abaxial and adaxial lighter than RHS 155D.

Androecium:

*Filaments*.—Five, thin, about 2.0 mm long and less than 0.5 mm in diameter; color white, lighter than RHS N155D.

*Anthers*.—Basifixed; oblong to about 0.5 mm long and about 0.2 mm wide; color nearest RHS 23A.

*Pollen*.—Not observed under present conditions.

Gynoecium:

*Pistil*.—One central two-beaked pistil.

*Style*.—About 6.0 mm long and 0.2 mm at apex flaring to 2.0 mm at base; color white lighter than RHS 155D.

*Stigma*.—Minute, about 0.2 mm diameter; color nearest RHS 155D.

*Ovary*.—Two carpels; ovoid, apex tapering to meet style; rounded base and sides; about 2.0 mm across at base and 2.5 mm tall; color nearest RHS 155D.

Fruit and seed: Not observed.

Disease and pest tolerance: ×*Heucherella* 'Hopscotch' grows best with ample moisture and good drainage in part shade or protection from sun in the hottest part of the day. Cold hardy from USDA zones 4 to 9. ×*Heucherella* 'Hopscotch' is able to tolerate heat and humidity better than many ×Heucherella. Other pest and disease resistance and tolerance outside of that normal for ×*Heucherella* is not known.

It is claimed:

1. A new and distinct ornamental ×*Heucherella* plant named 'Hopscotch' as herein illustrated and described.

* * * * *